: US 7,864,324 B2
(45) Date of Patent: Jan. 4, 2011

(12) United States Patent
Shyu et al.

(54) REFLECTIVE SCATTEROMETER

(75) Inventors: Deh-Ming Shyu, Miaoli County (TW); Yi-Sha Ku, Hsinchu (TW); Sen-Yih Chou, Taipei (TW); Shu-Ping Dong, Taichung County (TW); Wei-Te Hsu, Taipei County (TW)

(73) Assignee: Industrial Technology Research Institute, Hsin-Chu (TW)

( * ) Notice: Subject to any disclaimer, the term of this patent is extended or adjusted under 35 U.S.C. 154(b) by 234 days.

(21) Appl. No.: 12/352,069

(22) Filed: Jan. 12, 2009

(65) Prior Publication Data
US 2010/0053627 A1 Mar. 4, 2010

(30) Foreign Application Priority Data
Sep. 2, 2008 (TW) .............................. 97133614 A

(51) Int. Cl.
*G01N 21/47* (2006.01)
(52) U.S. Cl. ..................................................... 356/446
(58) Field of Classification Search ......... 356/445–448, 356/450–458
See application file for complete search history.

(56) References Cited
U.S. PATENT DOCUMENTS 4,988,205 A * 1/1991 Snail ........................... 356/446
5,912,741 A * 6/1999 Carter et al. ................. 356/445
6,744,505 B1 * 6/2004 Wang et al. .................. 356/326
6,768,567 B2 * 7/2004 Naulleau ...................... 359/15
6,987,568 B2 1/2006 Dana
7,292,341 B2 * 11/2007 Brill et al. .................... 356/445
7,656,519 B2 * 2/2010 Meeks et al. .............. 356/237.2

* cited by examiner

*Primary Examiner*—Gregory J Toatley
*Assistant Examiner*—Jarreas C Underwood
(74) *Attorney, Agent, or Firm*—Tim Tingkang Xia; Morris, Manning & Martin, LLP

(57) ABSTRACT

A reflective scatterometer capable of measuring a sample is provided. The reflective scatterometer includes a paraboloid mirror, a light source, a first reflector, a second reflector and a detector. The paraboloid mirror has an optical axis and a parabolic surface, wherein the sample is disposed on the focal point of the parabolic surface and the normal direction of the sample is parallel with the optical axis. A collimated beam generated from the light source is reflected by the first reflector to the parabolic surface and then is reflected by the parabolic surface to the sample to form a first diffracted beam. The first diffracted beam is reflected by the parabolic surface to the second reflector and is then reflected by the second reflector to the detector.

20 Claims, 7 Drawing Sheets

US 7,864,324 B2

REFLECTIVE SCATTEROMETER

CROSS-REFERENCE TO RELATED APPLICATIONS

This non-provisional application claims priority under 35 U.S.C. §119(a) on Patent Application No. 097133614 filed in Taiwan on Sep. 2, 2008, the entire contents of which are hereby incorporated by reference.

BACKGROUND OF THE INVENTION

1. Field of the Invention

The present invention generally relates to a scatterometer and, more particularly, to a reflective scatterometer.

2. Background of the Invention

The scatterometer plays a key role in measuring critical dimension in the semiconductor industry. As the critical dimension of semiconductor processing is shrinking down, it gets more and more difficult to measure overlay error between layers by conventional optical microscope or to measure the line width by scanning electron microscope (SEM). Therefore, the scatterometer system using of diffraction optics of fine lines and overlay structures by gratings has attracted tremendous attention.

Since the scatterometer exhibits excellent repeatability, reproducibility and optical non-destructive and high throughput measuring, the scatterometer has become important in semiconductor technology. Generally, the scatterometer can be divided into the spectrum scatterometer and the angular scatterometer.

In the spectrum scatterometer, the incoming beam is perpendicularly incident on a sample to measure the perpendicularly reflected zero-order diffracted beam. By setting up a measured reflectivity signature of the incoming beam with different wavelengths and comparing the measured reflectivity signature to the theoretically derived reflectivity signature, it can be determined whether the grating structure is defective. However, perpendicularity is not an optimal incident angle, which results in poor measuring sensitivity of the spectrum scatterometer. Moreover, the refractive index of a material at different wavelengths must be known before the theoretical reflectivity signature can be derived.

In the angular scatterometer, the angle of the incoming beam incident on a sample is changed and the zero-order diffracted beam is measured corresponding to different incident angles. By setting up a measured reflectivity signature of the incoming beam with different incident angles and comparing the measured reflectivity signature to the theoretically derived reflectivity signature, it can be determined whether the grating structure is defective. However, the angular scatterometer is usually complicated and is described with reference to accompanying drawings.

FIG. 1 is a structural diagram of a conventional reflective scatterometer, which is disclosed in U.S. Pat. No. 5,703,692. Referring to FIG. 1, the conventional reflective scatterometer 100 is capable of measuring the grating structure (periodic structure) on a sample 50. The reflective scatterometer 100 comprises a light source 110, a rotating block 120, a beam splitter 130, a focusing lens 140 and a detector 150. The light source 110 generates a collimated beam 112, which is incident on the beam splitter 130 after passing through the rotating block 120. The sample 50 is disposed at the focal point of the focusing lens 140. The collimated beam 112 is focused on the sample 50 after being reflected by the beam splitter 130 and passing through focusing lens 140 so as to generate a diffracted beam 114, which is zero-order diffracted.

Accordingly, the diffracted beam 114 is received by the detector 150 after passing through the focusing lens 140 and the beam splitter 130 so that the intensity of the diffracted beam 114 can be measured. Moreover, the rotating angle of the rotating block 120 is adjusted to translate the collimated beam 112 to change the incident angle of the collimated beam 112 on the sample 50. Therefore, the reflectivity can be measured corresponding to different incident angles to determine whether the sample 50 is defective.

FIG. 2 is a structural diagram of another conventional reflective scatterometer, which is disclosed in U.S. Pat. No. 6,987,568. Referring to FIG. 2, the conventional reflective scatterometer 200 is capable of measuring the grating structure on a sample 50. The reflective scatterometer 200 comprises a light source 210, an aperture 220, a beam splitter 230, a parabolic reflector 240 and a detector 250. The parabolic reflector 240 has an optical axis 242. The sample 50 is disposed at the focal point of the parabolic reflector 240 and the normal direction 52 of the sample 50 is perpendicular to the optical axis 242.

Accordingly, a collimated beam 212 generated by the light source 210 is reflected by the beam splitter 230 onto the parabolic reflector 240 after passing through the aperture 220. The collimated beam 212 is then reflected by the parabolic reflector 240 onto the sample 50 to generate a diffracted beam 214, which is zero-order diffracted. The diffracted beam 214 is reflected by the parabolic reflector 240 to pass through the beam splitter 230 to be received by the detector 250 so that the intensity of the diffracted beam 214 can be measured. Moreover, the location of the aperture 220 is adjusted to translate the collimated beam 212 to change the incident angle of the collimated beam 212 on the sample 50. Therefore, the reflectivity can be measured corresponding to different incident angles to determine whether the sample 50 is defective.

SUMMARY OF THE INVENTION

In one exemplary embodiment, the present invention provides a reflective scatterometer capable of measuring a sample, the reflective scatterometer comprising: a paraboloid mirror with an optical axis and a parabolic surface; a light source capable of generating a collimated beam; a first reflector capable of reflecting the collimated beam onto the parabolic surface capable of reflecting the collimated beam onto the sample so as to generate a first diffracted beam; a second reflector capable of reflecting the first diffracted beam reflected by the parabolic surface; and a detector capable of receiving the first diffracted beam reflected by the second reflector.

In another exemplary embodiment for multi-order diffracted beam reflected from the sample. An example for first-order and second-order beams reflected from the sample is shown below; the present invention provides a reflective scatterometer capable of measuring a sample, the reflective scatterometer comprising: a paraboloid mirror with an optical axis and a parabolic surface; a light source capable of generating a collimated beam; a first reflector capable of reflecting the collimated beam onto the parabolic surface capable of reflecting the collimated beam onto the sample so as to generate a first diffracted beam and a second diffracted beam; and a first detector capable of receiving the first diffracted beam and the second diffracted beam reflected by the parabolic surface.

BRIEF DESCRIPTION OF THE DRAWINGS

The objects and spirits of various embodiments of the present invention will be readily understood by the accompanying drawings and detailed descriptions, wherein.

DETAILED DESCRIPTION OF THE PREFERRED EMBODIMENT

The present invention provides a reflective scatterometer capable of performing large-angle and multi-wavelength scanning with an additional viewing window to precisely control the position where the collimated beam is incident on the sample to improve measuring reliability.

Moreover, the present invention further provides a reflective scatterometer capable of simultaneously measuring the zero-order diffracted beam and the multi-order diffracted beam.

Accordingly, in the reflective scatterometer of the present invention, the normal direction of the sample is disposed parallel with the optical axis of the paraboloid mirror so as to increase the incident angle of the collimated beam incident on the sample to perform large-angle scanning. Moreover, by using the viewing window to precisely control the position where the collimated beam is incident on the sample to improve measuring reliability. Furthermore, the reflective scatterometer is capable of simultaneously measuring the zero-order diffracted beam, the first-order diffracted beam and the second-order diffracted beam for real-time comparison to enhance the measuring efficiency.

First Exemplary Embodiment

Figure 1:
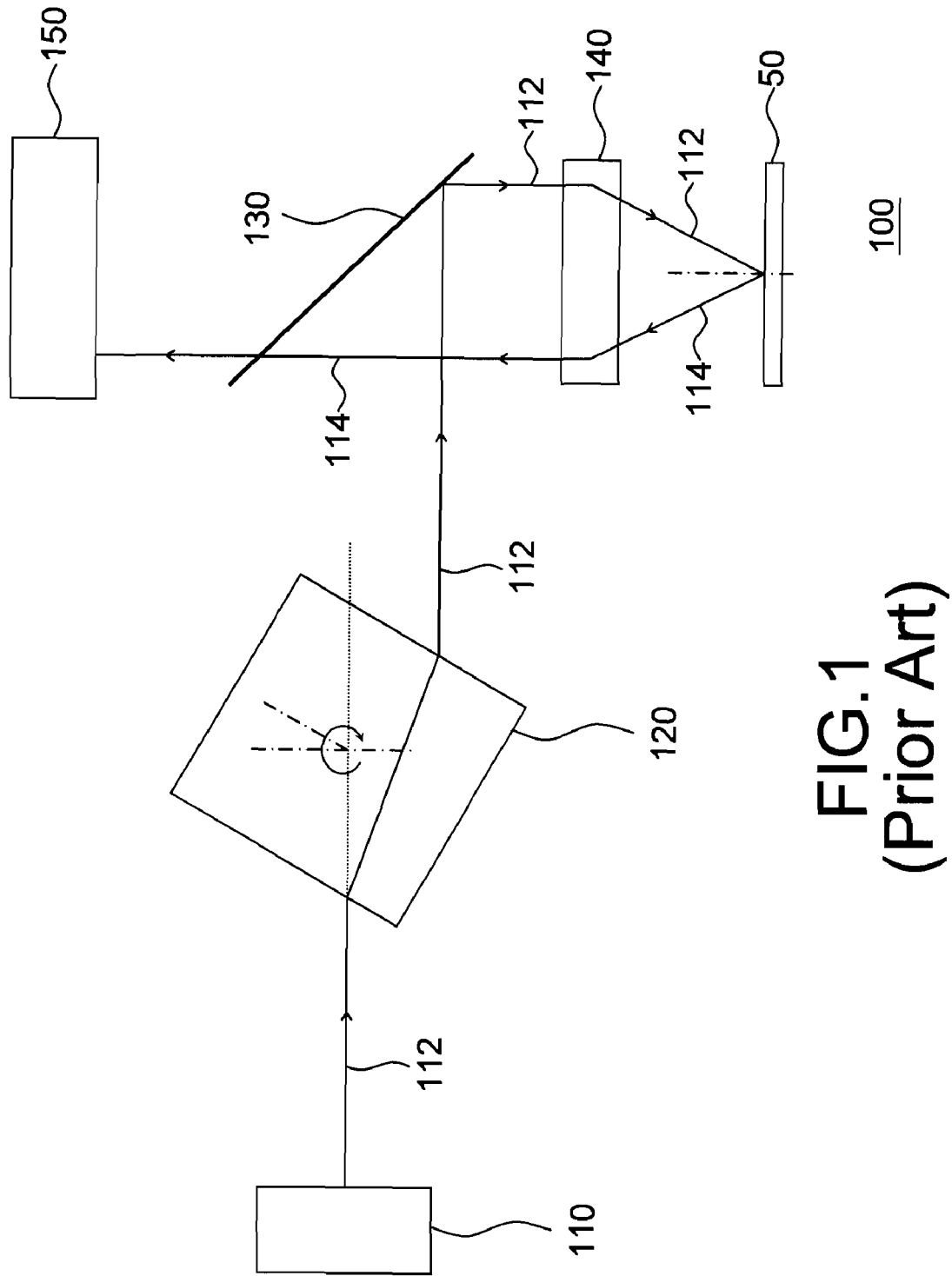
FIG. 1 is a structural diagram of a conventional reflective scatterometer.
Figure 2:
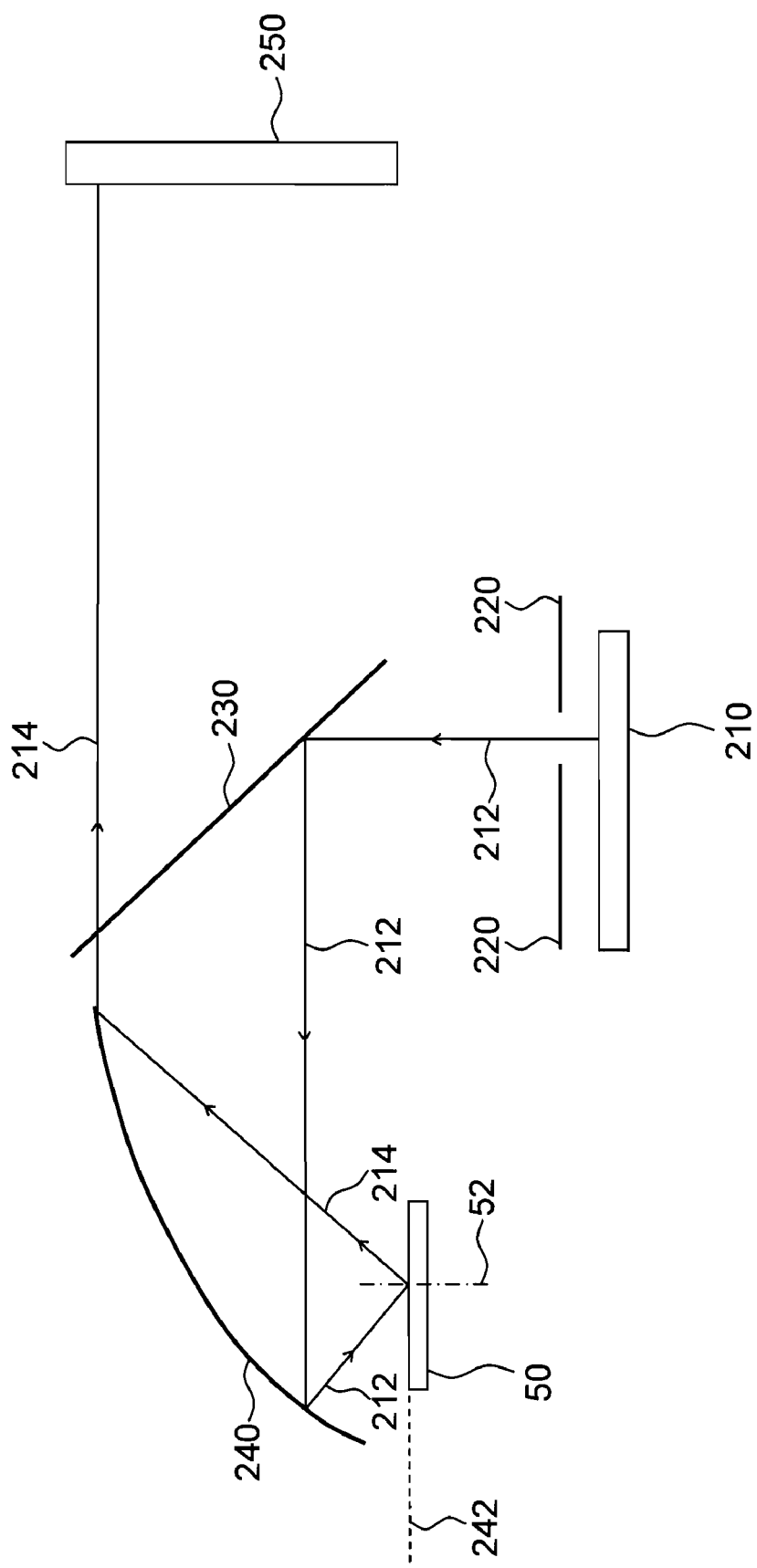
FIG. 2 is a structural diagram of another conventional reflective scatterometer.
Figure 3A:
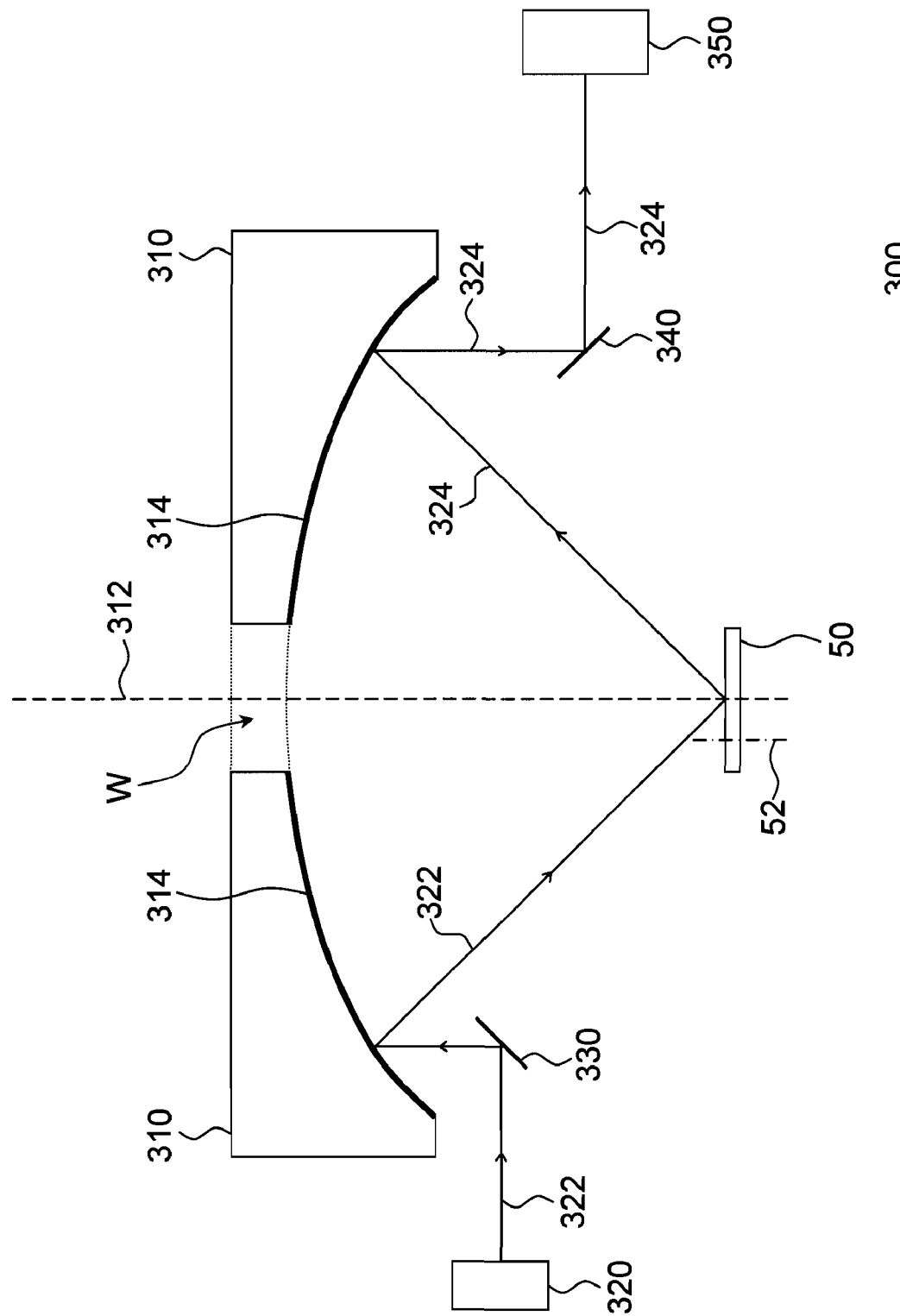
FIG. 3A and FIG. 3B are structural diagrams of a reflective scatterometer according to the first exemplary embodiment of the present invention.
Figure 3B:
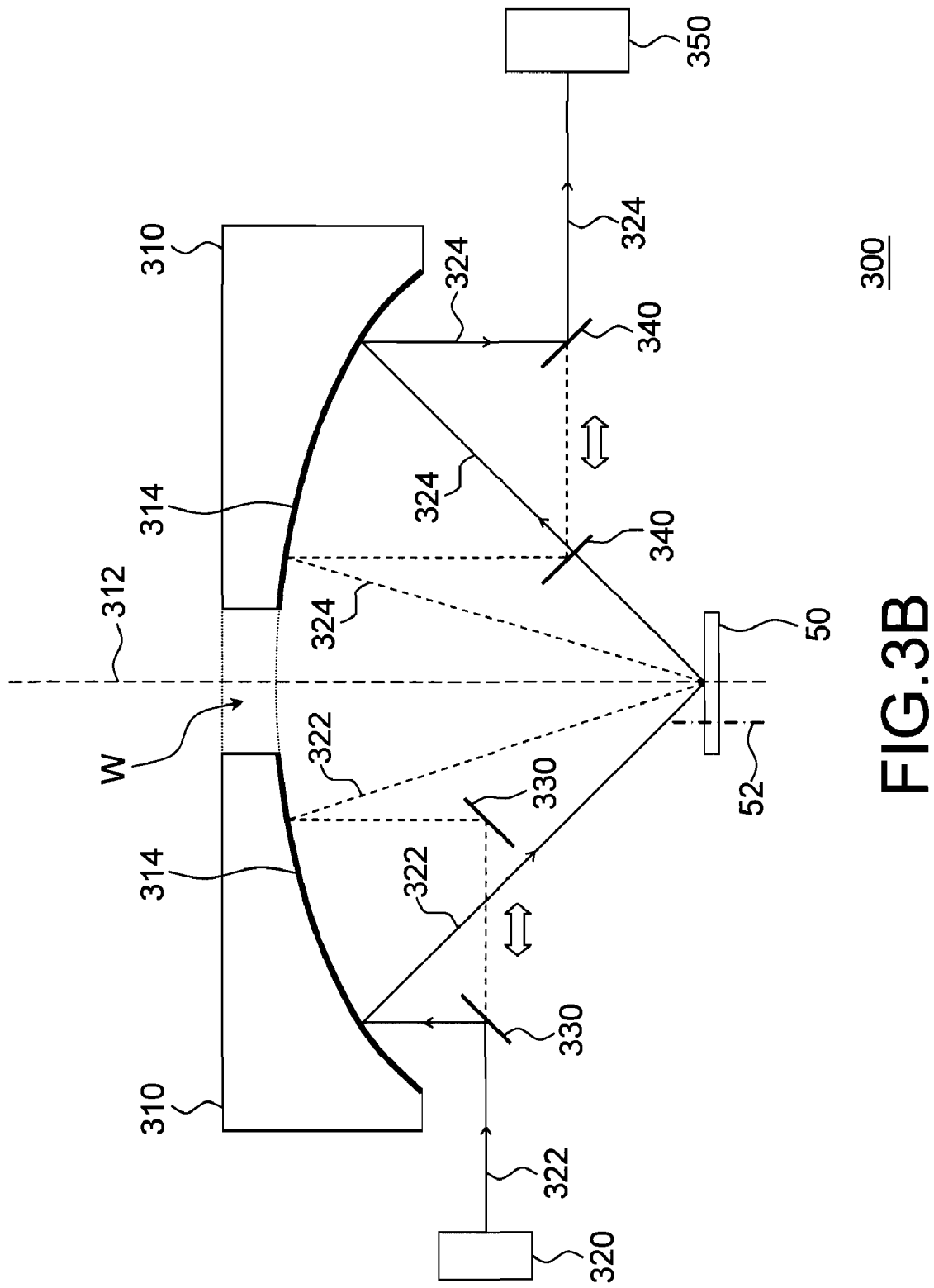

FIG. 3A and FIG. 3B are structural diagrams of a reflective scatterometer according to the first exemplary embodiment of the present invention. In FIG. 3B, a dotted line represents the optical path after the some components have been moved. Referring to FIG. 3A and FIG. 3B, the reflective scatterometer 300 is capable of measuring a sample 50, more particularly, the periodic structure (such as the grating structure) on the sample 50. Moreover, the sample 50 is, for example, a silicon substrate or a glass substrate. However, the present invention is neither limited to the examples of the sample 50 nor the structure on the sample 50.

Accordingly, the reflective scatterometer 300 comprises a paraboloid mirror 310, a light source 320, a first reflector 330, a second reflector 340 and a detector 350. The present invention is characterized by the arrangement of the sample 50 corresponding to the paraboloid mirror 310. More particularly, the paraboloid mirror 310 has an optical axis 312 and a parabolic surface 314. The sample 50 is disposed at the focal point of the parabolic surface 314 and the normal direction 52 of the sample 50 is parallel with the optical axis 312. Therefore, any light beam that is parallel with the optical axis 312 is reflected to pass through the focal point of the parabolic surface 314 (where the sample 50 is located) after being incident on the parabolic surface 314. On the contrary, any light beam that passes through the focal point of the parabolic surface 314 is reflected to travel in parallel with the optical axis 312 after being incident on the parabolic surface 314.

Further referring to FIG. 3A and FIG. 3B, in the present invention, the first reflector 330 is used to adjust the direction of the collimated beam 322 so that the collimated beam 322 is parallel with the optical axis 312 before being incident on the parabolic surface 314. Thereby, the collimated beam 322 is reflected by the parabolic surface 314 to reach the sample 50.

In the present embodiment, the angle between the first reflector 330 and the optical axis 312 is, for example, 45°, and the optical path of the collimated beam 322 from the light source 320 is perpendicular to the optical axis 312. Therefore, the collimated beam 322 is reflected by the first reflector 330 by 90°. In other words, the optical path of the collimated beam 322 is perpendicular to the optical axis 312 before being incident on the first reflector 330, while the optical path of the collimated beam 322 is parallel with the optical axis 312 after being reflected by the first reflector 330.

With such an arrangement, the first reflector 330 of the present invention is moved perpendicularly to the optical axis 312 (as shown in FIG. 3B) to change the position where the collimated beam 322 is incident onto the parabolic surface 314 so as to adjust the incident angle of the collimated beam 322 incident onto the sample 50. In other words, the present invention uses a step motor or other mechanism to control the location of the first reflector 330 to adjust the incident on angle of the collimated beam 322.

After the collimated beam 322 is incident on the sample 50, the collimated beam 322 is diffracted by the sample 50 to generate the first diffracted beam 324. In the present embodiment, the first diffracted beam 324 is, for example, zero-order diffracted beam. Therefore, the outcoming angle of the first diffracted beam 324 is equal to the incident angle of the collimated beam 322. Moreover, since the first diffracted beam 324 is generated at the focal point of the parabolic surface 314, the optical path of the first diffracted beam 324 is parallel with the optical axis 324 after being reflected by the parabolic surface 314.

In the present invention, a second reflector 340 is disposed to reflect the first diffracted beam 324 onto detector 350. In the present embodiment, the angle between the second reflector 340 and the optical axis 312 is 45°, and the optical path between the detector 350 and the second reflector 340 is perpendicular to the optical axis 312. Therefore, the first diffracted beam 324 is reflected by the second reflector 340 by 90° to travel towards the detector 350. In other words, the optical path of the first diffracted beam 324 is parallel with the optical axis 312 after being reflected by the parabolic surface 314, while the optical path of the first diffracted beam 324 is perpendicular to the optical axis 312 after being incident onto the detector 350.

Similarly, the second reflector 340 of the present invention is moved perpendicularly to the optical axis 312 (as shown in FIG. 3B) so as to reflect the first diffracted beam 324 onto the detector 350. In other words, the present invention uses a step motor to control the location of the second reflector 340 so that the detector 350 is able to receive the first diffracted beam 324 without moving the paraboloid mirror 310 or the detector 350.

With such an arrangement, the reflective scatterometer 300 of the present embodiment is capable of performing large-angle scanning of about 70° without generating color deviation.

In the present embodiment, the light source 320 is a multi-wavelength light source. Therefore, the reflective scatterometer 300 of the present invention is capable of performing scanning based on the wavelength and the angle to measure data. Moreover, the detector 350 is, for example, a power meter to receive the first diffracted beam 324 to determine the reflectivity signature to determine whether the sample 50 is defective. Moreover, the paraboloid mirror 310 is, for example, a spherical paraboloid mirror. However, the present invention is not limited to the type of the paraboloid mirror 310, the detector 350 and the light source 320. For example, the paraboloid mirror 310 can also be a cylindrical paraboloid mirror, the detector 350 can be a complementary metal-oxide semiconductor (CMOS) device, and the light source 320 can be a HeNe laser or a light emitting diode (LED).

It is also noted that the light source 320, the previous described arrangement of the first reflector 330, the second reflector 340 and the detector 350 is only used to exemplify the present invention. In the present invention, the light source 320 and the first reflector 330 are disposed so that the optical path of the collimated beam 322 is parallel with the optical axis 312 before it is incident on the parabolic surface 314, while the second reflector 340 and the detector 350 are disposed so that the optical path of the first diffracted beam 324 parallel with optical axis 312 is received by the detector 350 after being reflected by the second reflector 340. However, the reflective scatterometer of the present invention is not limited to the structure as aforementioned.

Figure 3C:
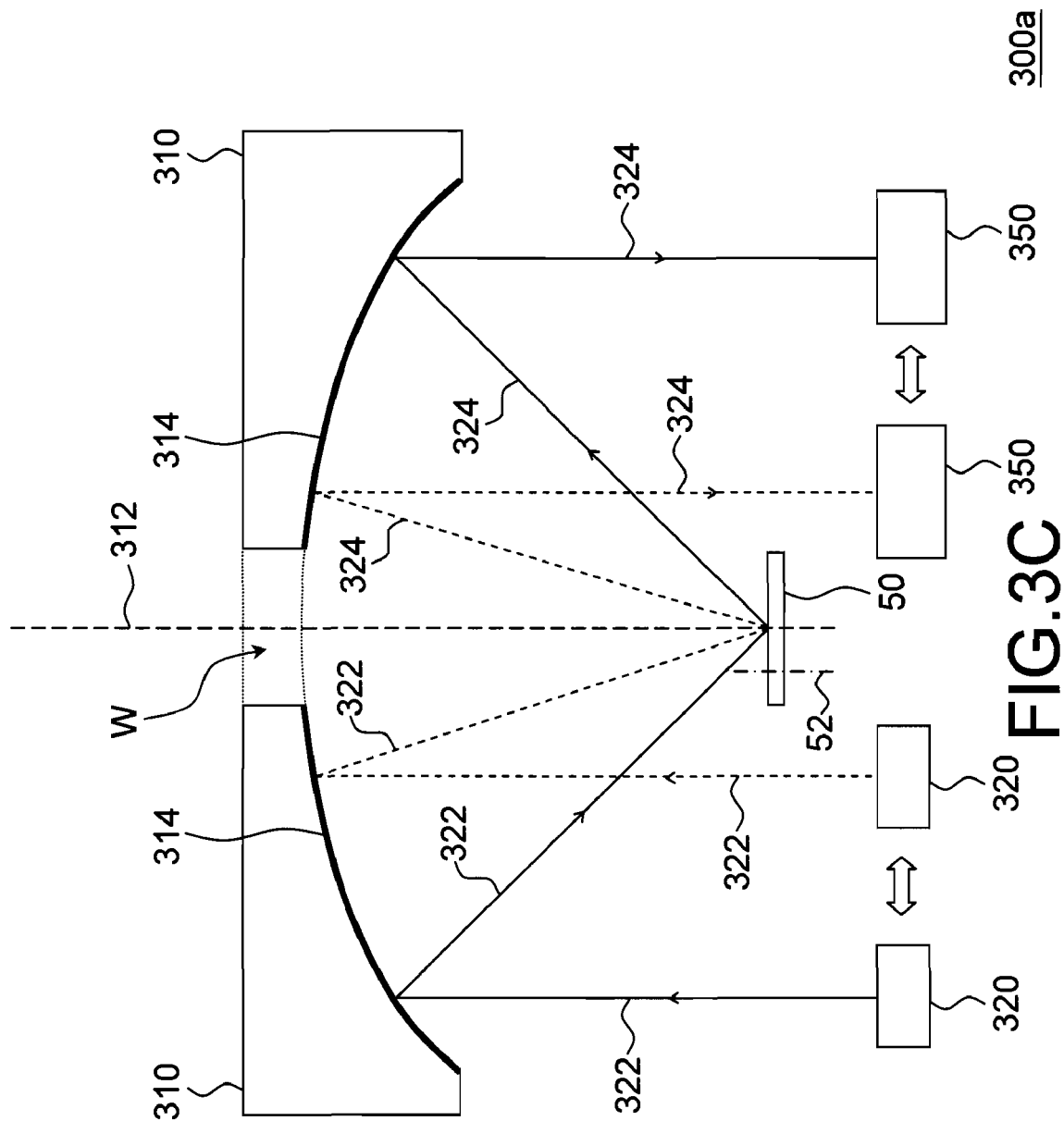
FIG. 3C is a structural diagram of another reflective scatterometer according to the first exemplary embodiment of the present invention.

FIG. 3C is a structural diagram of another reflective scatterometer according to the first exemplary embodiment of the present invention. In FIG. 3C, a dotted line represents the optical path after the some components have been moved. Referring to FIG. 3C, the reflective scatterometer 300a is similar to the previous reflective scatterometer 300 (in FIG. 3B) except that the reflective scatterometer 300a does not comprise the first reflector 330 and the second reflector 340. In the reflective scatterometer 300a, the light source 320 emits the collimated beam 322 parallel with the optical axis 312 onto the parabolic surface 314 and the detector 350 receives the first diffracted beam 324 parallel with the optical axis 312.

As previous described, the light source 320 is moved perpendicularly to the optical axis 312 so as to change the position where the collimated beam 322 is incident on the parabolic surface 314 to change the incident angle of the collimated beam 322 incident onto the sample 50. Moreover, in the present embodiment, the detector 350 is moved perpendicularly to the optical axis 312 so that the detector is capable of receiving the first diffracted beam 324 parallel with the optical axis 312. Generally, the light source 320 and the detector 350 are heavier than the first reflector 330 and the second reflector 340 so that the precision of the movement of the light source 320 and the detector 350 is smaller than the precision of the movement of the first reflector 330 and the second reflector 340.

As described above, the reflective scatterometer 300 can be used to improve the precision. Moreover, the optical path can be modified by anyone with ordinary skill in the art by changing some components within the scope of the present invention.

Referring to FIG. 3A and FIG. 3C, to precisely control the position where the collimated beam 322 is incident on the sample 50, the reflective scatterometer 300 and the reflective scatterometer 300a of the present embodiment further comprise a viewing window W disposed at the center of the paraboloid mirror 310. Moreover, an optical microscope is further disposed on the viewing window W so that the sample 50 can be monitored by the user through the viewing window W.

As described above, unlike the prior art being unable to identify the position where the collimated beam is incident on the sample, in the present invention, the position where the collimated beam 322 is incident on the sample 50 can be precisely adjusted so as to significantly enhance the measuring precision.

Generally, as the collimated beam 322 is diffracted by the sample 50, in addition to the first diffracted beam 324 being zero-order diffracted beam, first-order diffraction or multi-order diffraction may also occur. By measuring multi-order diffraction, the structure of the sample 50 can be further identified. In another embodiment for the measurement of first-order and second-order reflected beams described hereinafter, the measurement of first-order diffraction and second-order diffraction is described with accompanying drawings.

Second Exemplary Embodiment

Figure 4A:
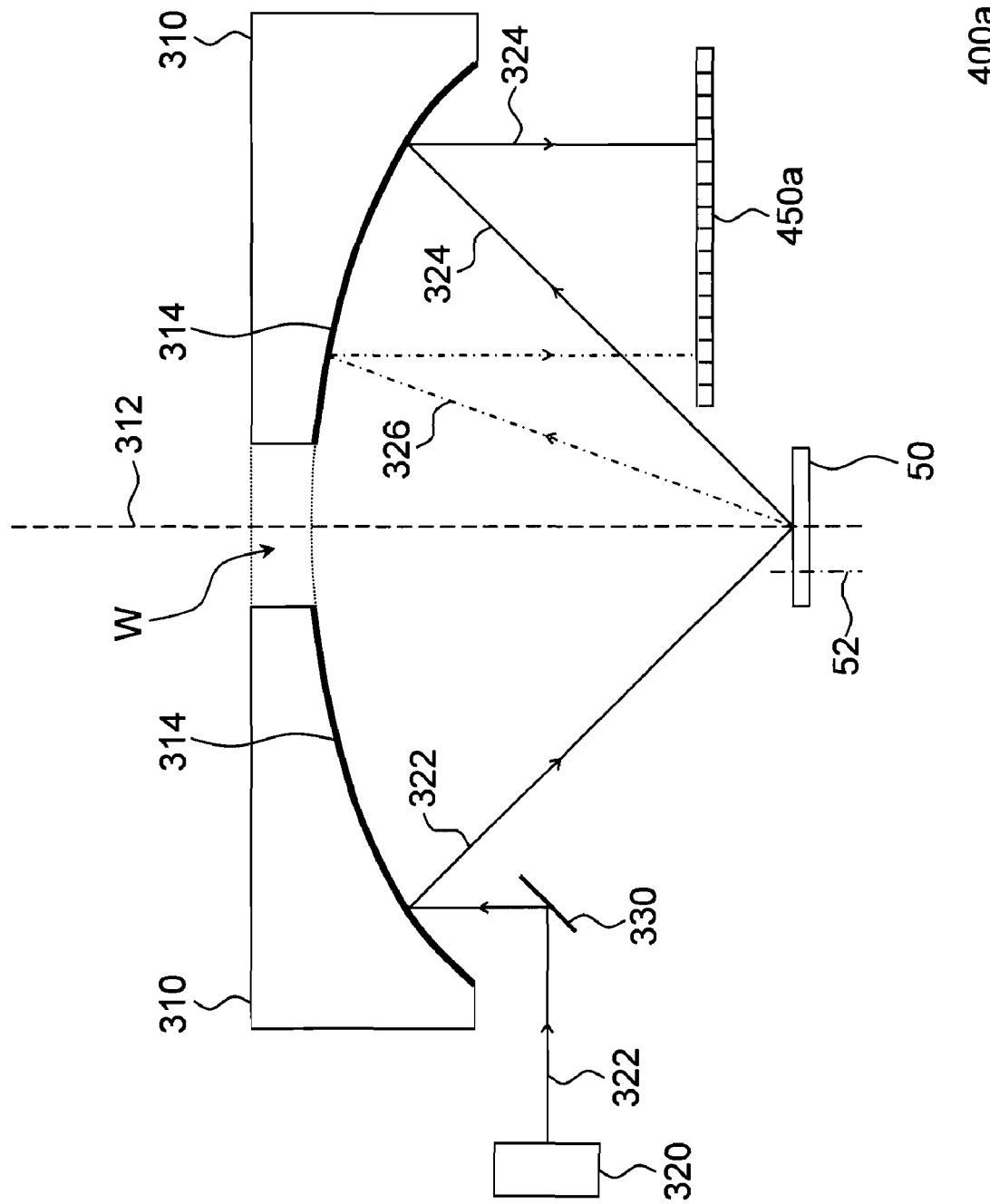
FIG. 4A is a structural diagram of a reflective scatterometer according to the second exemplary embodiment of the present invention.

FIG. 4A is a structural diagram of a reflective scatterometer according to the second exemplary embodiment of the present invention. Referring to FIG. 4A, the reflective scatterometer 400a of the present embodiment is similar to the aforementioned reflective scatterometer 300 (in FIG. 3A). For simplicity, similar components are denoted by identical labels except that the second reflector 340 and the detector 350 in the previous embodiment are replaced by the first detector 450a of the reflective scatterometer 400a.

More particularly, the first detector 450a is, for example, a linear charge-coupled device (linear CCD), and the normal direction of the first detector 450a is parallel with the optical axis 312 so as to receive the first diffracted beam 324 parallel with the optical axis 312. Moreover, the collimated beam 322 is incident on the sample 50 to generate the first diffracted beam 324 being zero-order diffracted and the second diffracted beam 326 being first-order diffracted. The second diffracted beam 326 is reflected by the parabolic surface 314 to be parallel with the optical axis 312 and vertically incident onto the first detector 450a.

The first detector 450a simultaneously receives the first diffracted beam 324 and the second diffracted beam 326 to acquire the reflectivity signature corresponding to different diffraction orders to enhance the efficiency of determining the structure of the sample 50. Certainly, second-order diffraction also occurs after the collimated beam 322 is incident on the sample 50, and therefore, a second detector can be added in the present invention, as described hereinafter.

Figure 4B:
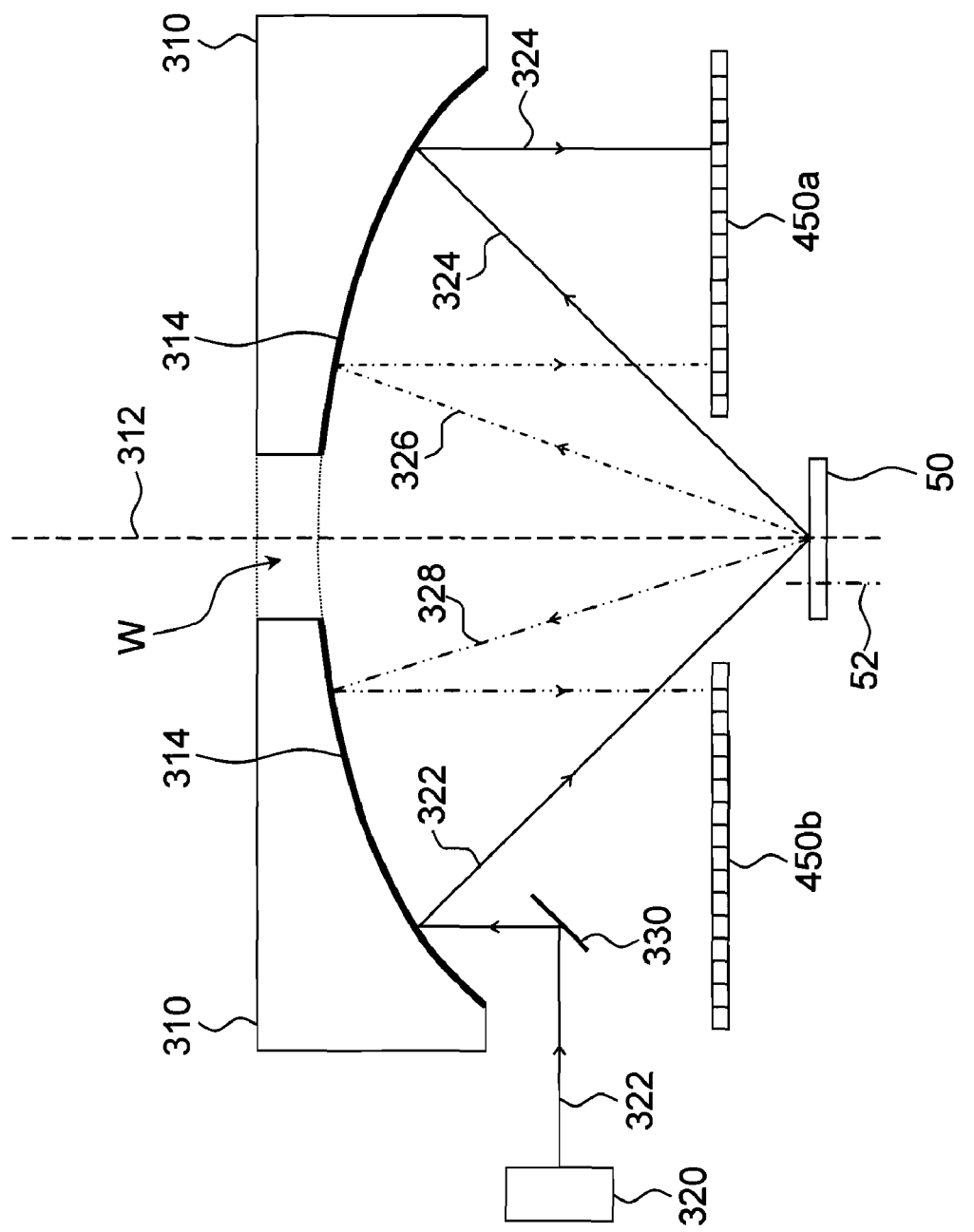
FIG. 4B is a structural diagram of another reflective scatterometer according to the second exemplary embodiment of the present invention.

FIG. 4B is a structural diagram of another reflective scatterometer according to the second exemplary embodiment of the present invention. Referring to FIG. 4B, the reflective scatterometer 400b in the present embodiment is similar to the previous reflective scatterometer 400a (in FIG. 4A) except that reflective scatterometer 400b further comprises a second detector 450b to receive a third diffracted beam 328, which is second-order diffracted after the collimated beam 322 is incident on the sample 50.

Similarly, the second detector 450b is also a linear charge-coupled device with the normal direction being parallel with the optical axis 312 to directly receive the third diffracted beam 328 parallel with the optical axis 312. In the present embodiment, the first diffracted beam 324, the second diffracted beam 326 and the third diffracted beam 328 can be simultaneously received to acquire the reflectivity signature corresponding to different diffraction orders to enhance the efficiency of determining the structure of the sample 50.

Accordingly, in the reflective scatterometer of the present invention, the normal direction of the sample is disposed parallel with the optical axis of the paraboloid mirror so as to increase the incident angle of the collimated beam incident on the sample to perform large-angle scanning.

The reflective scatterometer of an exemplary embodiment is capable of performing large-angle scanning of about 70° to acquire the reflectivity signature corresponding to different diffraction orders to determine the structure of the sample. Moreover, scanning corresponding to both the angle and the wavelength can be performed.

Moreover, by using the viewing window to precisely control the position where the collimated beam is incident on the sample to improve measuring reliability. The viewing window is disposed to identify the position where the collimated beam is incident on the sample to improve the measuring precision.

Furthermore, the reflective scatterometer is capable of simultaneously measuring the zero-order diffracted beam, the first-order diffracted beam and the second-order diffracted beam for real-time comparison to enhance the measuring efficiency. The multi-order diffraction can be simultaneously measured to acquire the reflectivity signature corresponding to different diffraction orders to enhance the efficiency of determining the structure of the sample.

Although this invention has been disclosed and illustrated with reference to particular exemplary embodiments, the principles involved are susceptible for use in numerous other embodiments that will be apparent to persons skilled in the art. This invention is, therefore, to be limited only as indicated by the scope of the appended claims.

What is claimed is:

1. A reflective scatterometer capable of measuring a sample, the reflective scatterometer comprising:
   a paraboloid mirror with an optical axis and a parabolic surface;
   a light source capable of generating a collimated beam;
   a first reflector capable of reflecting the collimated beam onto the parabolic surface capable of reflecting the collimated beam onto the sample so as to generate a first diffracted beam;
   a second reflector capable of reflecting the first diffracted beam reflected by the parabolic surface; and
   a detector capable of receiving the first diffracted beam reflected by the second reflector;
   wherein the normal direction of the sample is parallel with the optical axis and the sample is disposed at the focal point of the parabolic surface.

2. The reflective scatterometer as recited in claim 1, wherein the first reflector is moved perpendicularly to the optical axis so as to change the incident angle of the collimated beam incident on the sample.

3. The reflective scatterometer as recited in claim 2, wherein the optical path of the collimated beam before being incident on the first reflector is perpendicular to the optical axis, while the optical path of the collimated beam after being reflected by the first reflector is parallel with the optical axis.

4. The reflective scatterometer as recited in claim 1, wherein the second reflector is moved perpendicularly to the optical axis so as to reflect the first diffracted beam onto the detector.

5. The reflective scatterometer as recited in claim 4, wherein the optical path of the first diffracted beam after being reflected by the parabolic surface is parallel with the optical axis, while the optical path of the first diffracted beam after being reflected by the second reflector is perpendicular to the optical axis.

6. The reflective scatterometer as recited in claim 1, wherein the paraboloid mirror is a spherical paraboloid mirror.

7. The reflective scatterometer as recited in claim 1, wherein the paraboloid mirror has a viewing window disposed at the center of the paraboloid mirror.

8. The reflective scatterometer as recited in claim 1, wherein the detector is a power meter.

9. The reflective scatterometer as recited in claim 1, wherein the light source is a multi-wavelength light source.

10. The reflective scatterometer as recited in claim 1, wherein the first diffracted beam is zero-order diffracted.

11. A reflective scatterometer capable of measuring a sample, the reflective scatterometer comprising:
    a paraboloid mirror with an optical axis and a parabolic surface;
    a light source capable of generating a collimated beam;
    a first reflector capable of reflecting the collimated beam onto the parabolic surface capable of reflecting the collimated beam onto the sample so as to generate diffracted beams; and
    a first detector capable of receiving the diffracted beams reflected by the parabolic surface;
    wherein the normal direction of the sample is parallel with the optical axis and the sample is disposed at the focal point of the parabolic surface.

12. The reflective scatterometer as recited in claim 11, wherein the first reflector is moved perpendicularly to the optical axis so as to change the incident angle of the collimated beam incident on the sample.

13. The reflective scatterometer as recited in claim 12, wherein the optical path of the collimated beam before being incident on the first reflector is perpendicular to the optical axis, while the optical path of the collimated beam after being reflected by the first reflector is parallel with the optical axis.

14. The reflective scatterometer as recited in claim 11, wherein the first detector is a linear charge-coupled device with the normal direction parallel with the optical axis.

15. The reflective scatterometer as recited in claim 11, wherein the diffracted beams are multi-order diffracted beams.

16. The reflective scatterometer as recited in claim 11, wherein the paraboloid mirror is a spherical paraboloid mirror.

17. The reflective scatterometer as recited in claim 11, wherein the paraboloid mirror has a viewing window disposed at the center of the paraboloid mirror.

18. The reflective scatterometer as recited in claim 11, wherein the light source is a multi-wavelength light source.

19. The reflective scatterometer as recited in claim 11, further comprising a second detector being a linear charge-coupled device with the normal direction parallel with the optical axis.

20. The reflective scatterometer as recited in claim 19, wherein the parabolic surface reflects the collimated beam onto the sample to generate high-order diffraction beams to be reflected by the parabolic surface onto the second detector.

* * * * *